United States Patent
Dinakara et al.

(10) Patent No.: US 10,813,787 B2
(45) Date of Patent: Oct. 27, 2020

(54) OSTOMY MANAGEMENT DEVICE

(71) Applicant: SECRETARY, DEPARTMENT OF BIOTECHNOLOGY, New Delhi (IN)

(72) Inventors: Deevish Dinakara, Bangalore (IN); Neeraj Kumar, Noida (IN); Pranav Chopra, New Delhi (IN); Sohail Gupta, Panchkula (IN); Balram Bhargava, New Delhi (IN); Anil Agarwal, New Delhi (IN)

(73) Assignee: SECRETARY, DEPARTMENT OF BIOTECHNOLOGY, New Dehli (IN)

( * ) Notice: Subject to any disclaimer, the term of this patent is extended or adjusted under 35 U.S.C. 154(b) by 356 days.

(21) Appl. No.: 15/534,865

(22) PCT Filed: Dec. 11, 2015

(86) PCT No.: PCT/IB2015/059545
§ 371 (c)(1),
(2) Date: Jun. 9, 2017

(87) PCT Pub. No.: WO2016/092519
PCT Pub. Date: Jun. 16, 2016

(65) Prior Publication Data
US 2017/0367871 A1    Dec. 28, 2017

(30) Foreign Application Priority Data
Dec. 12, 2014 (IN) ............ 3697/DEL/2014

(51) Int. Cl.
*A61F 5/44* (2006.01)
*A61F 5/445* (2006.01)

(52) U.S. Cl.
CPC ............ *A61F 5/4408* (2013.01); *A61F 5/445* (2013.01); *A61F 5/4404* (2013.01); *A61F 5/4407* (2013.01); *A61F 2005/4455* (2013.01)

(58) Field of Classification Search
CPC combination set(s) only.
See application file for complete search history.

(56) References Cited

U.S. PATENT DOCUMENTS 6,033,390 A * 3/2000 von Dyck ............... A61F 5/441
600/29
7,258,661 B2 * 8/2007 Davies ................... A61F 5/445
600/32

(Continued)

FOREIGN PATENT DOCUMENTS

WO    199943277    9/1999
WO    2008103788   8/2008

(Continued)

OTHER PUBLICATIONS

International Search Report—Corresponding PCT Application No. PCT/IB2015/059545, dated Apr. 18, 2016, 5 pages.

*Primary Examiner* — Guy K Townsend
(74) *Attorney, Agent, or Firm* — Cozen O'Connor

(57) ABSTRACT

An ostomy management device (100) including an ostomy port (102) insertable inside a stoma (202) on a patient's abdomen. The ostomy port (102) includes an outer flange (204) placed at periphery of the stoma (202). The outer flange (204) includes a collapsible chamber (210) to collect instilling fluid in a non-operating state of the outer flange (204). A fixation element (208) to anchor the ostomy management device (100) inside an intestine (214). The fixation element (208) is to expand after displacement of the instilling fluid contained in the outer flange (204) to the fixation element (208). An intermediate channel (206) to transport body waste to the stoma (202). A stoma plug (106), attached to the outer flange (204), to cover an opening in the outer flange (204) to stop the body waste from flowing out from the stoma (202) during an operating state of the outer flange (204).

11 Claims, 9 Drawing Sheets

(56) References Cited

U.S. PATENT DOCUMENTS

| | | | | |
|---|---|---|---|---|
| 8,858,520 B2* | 10/2014 | Gregory | ............... | A61F 5/445 |
| | | | | 604/346 |
| 8,939,952 B2* | 1/2015 | Weig | ............... | A61F 5/445 |
| | | | | 604/355 |
| 9,339,646 B2* | 5/2016 | Ollivier | ............... | A61N 1/056 |
| 10,045,877 B2* | 8/2018 | Weig | ............... | A61F 5/445 |
| 2006/0058576 A1* | 3/2006 | Davies | ............... | A61F 5/445 |
| | | | | 600/32 |
| 2008/0015405 A1* | 1/2008 | Davies | ............... | A61F 5/445 |
| | | | | 600/32 |
| 2010/0022976 A1* | 1/2010 | Weig | ............... | A61F 2/0027 |
| | | | | 604/355 |
| 2010/0069859 A1* | 3/2010 | Weig | ............... | A61F 2/0027 |
| | | | | 604/335 |
| 2010/0174253 A1* | 7/2010 | Cline | ............... | A61F 5/445 |
| | | | | 604/328 |
| 2011/0040231 A1* | 2/2011 | Gregory | ............... | A61F 5/445 |
| | | | | 604/8 |
| 2011/0092929 A1* | 4/2011 | Weig | ............... | A61F 5/445 |
| | | | | 604/338 |
| 2012/0136423 A1* | 5/2012 | Ollivier | ............... | A61N 1/0563 |
| | | | | 607/126 |

FOREIGN PATENT DOCUMENTS

| | | | | |
|---|---|---|---|---|
| WO | WO-2008103788 A1 * | 8/2008 | ............ | A61F 5/451 |
| WO | 2008157172 | 12/2008 | | |
| WO | 2009131992 | 10/2009 | | |
| WO | 2009155537 | 12/2009 | | |
| WO | WO-2009155537 A1 * | 12/2009 | ............ | A61F 5/445 |
| WO | 2011007355 | 1/2011 | | |
| WO | 2011138727 | 11/2011 | | |

\* cited by examiner

OSTOMY MANAGEMENT DEVICE

TECHNICAL FIELD

The present subject matter relates to, a medical device and, in particular, to an ostomy management device.

BACKGROUND

Many people need to undergo ostomy surgery of bowel to treat a variety of gastrointestinal conditions. Ostomy is a surgical procedure that reroutes the normal movement of body wastes, such as stool out of the body. During ostomy surgery of the bowel, an opening is created in the abdomen. A portion of the bowel is brought to skin surface on the abdomen, such that the portion protrudes out from the opening. The protruding portion of the bowel is called a stoma. The stoma allows the body waste to exit from the body. Examples of ostomy surgery include ileostomy surgery and colostomy surgery.

BRIEF DESCRIPTION OF DRAWING

The detailed description is described with reference to the accompanying figures. In the figures, the left-most digit(s) of a reference number identifies the figure in which the reference number first appears. The same numbers are used throughout the drawings to reference like features and components.

DETAILED DESCRIPTION

Figure 1:
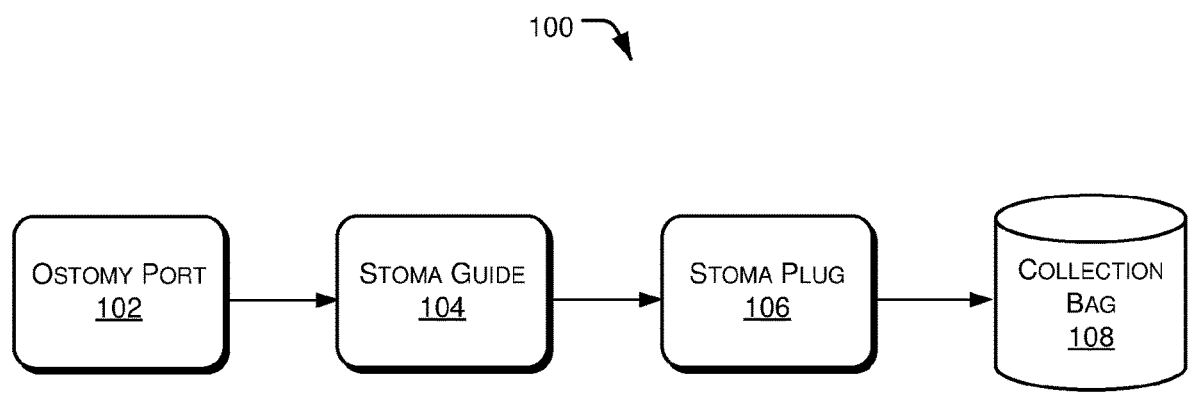
FIG. 1 illustrates a block diagram of an ostomy management device, in accordance with an embodiment of the present subject matter.

Ostomy is a surgical procedure performed to reroute the normal movement of body wastes, such as stool out of the body. During ostomy surgery of the bowel of a patient, a stoma is created to divert the flow of the body wastes. Once the stoma is created surgically, the patient loses control over moving the body wastes out from the body. Accordingly, a removable bag is attached around the stoma to constantly collect the body wastes. The removable bag is emptied as required. For example, the removable bag may be emptied several times a day depending on the type of ostomy surgery, diet, and the like. In one example, the removable bag may be attached to the stoma using an adhesive material. Such a removable bag may be referred to as an adhesive backed bag.

However, the patient may face problems because of lack of control over evacuation of the body waste. Further, having the removable bag attached to the stoma may affect peristomal skin, i.e., the skin surrounding a stoma on the outside surface of the abdomen. For instance, the peristomal skin may get exposed to body wastes and other intestinal contents, thus leading to peristomal skin irritation. Further, the use of strong adhesives may also cause peristomal skin irritation. The peristomal skin irritation often results in severe erosion, bleeding, discomfort, increased healthcare costs, and several other medical complications.

The present subject matter describes a medical device, also referred to as an ostomy management device that may be used by patients who have undergone ostomy surgery to manage body wastes. In an embodiment, the ostomy management device includes an ostomy port that can be inserted into a stoma on a patient's abdomen. The ostomy port is adapted to provide a protective sleeve on an inner side of intestine of the patient. The ostomy management device further includes a stoma plug that can be used to cover an opening in the ostomy port once the ostomy port has been placed inside the intestine. Covering the opening helps in preventing the body waste from continuously coming out of the stoma, through the ostomy port, thus avoiding the need of continuous attachment of a collection bag to the ostomy port.

In accordance to an embodiment of the present subject matter, the ostomy port includes an outer flange, an intermediate channel, and a fixation element. The outer flange is positioned outside the patient's body at a distal end of the ostomy port, i.e., the end away from the patient's centre of body. The outer flange is placed on periphery of the stoma when the ostomy port is inserted in the stoma. The fixation element is positioned inside the patient's body at a proximal end of the ostomy port, i.e., the end towards the patient's centre of body. The fixation element is to anchor the ostomy management device inside patient's abdomen walls. The intermediate channel connects the fixation element to the outer flange.

In one implementation, the outer flange includes a collapsible chamber to collect instilling fluid in a non-operating state of the outer flange. Compressing the outer flange displaces the instilling fluid to the fixation element to anchor the ostomy management device in the intestine. The fixation element is an expandable element that may expand upon displacement of the instilling fluid from the outer flange to the fixation element once the ostomy port is inserted in the abdomen. Anchoring the ostomy port helps preventing the ostomy management device from coming off while in use. Once the ostomy port is anchored in the intestine, the stoma plug may be used to cover an opening in the ostomy port. The ostomy management device may then be considered to be in an operating state during which the intermediate channel may transport body waste out from the intestine to the stoma.

In operation, to place the ostomy management device, the patient may hold the ostomy port with a stoma guide and gently insert a tip of the stoma guide protruding through the ostomy port into a stoma opening on an abdomen of the patient. Once the ostomy port is placed, the patient may retract the stoma guide leaving the ostomy port behind. The patient may then compress the outer flange to displace the instilling fluid to the fixation element through an instilling fluid pathway connecting the collapsible chamber to the fixation element. In one implementation, the instilling fluid pathway may be provided in the intermediate channel. Further, once the instilling fluid is displaced out of the outer flange, the outer flange is locked in its compressed state so that the instilling fluid does not escape out of the fixation element. As the instilling fluid enters the fixation element, the fixation element expands from a deflated state to an inflated state, thus anchoring ostomy port in the abdomen. The patient may subsequently put the stoma plug over an opening provided in the outer flange to close the ostomy port. Closing the stoma plug helps preventing the body waste from coming out of the outer flange in an operating state of the ostomy management device. To evacuate the body waste, the patient may connect the collection bag to the outer flange and then open the stoma plug to allow the body waste to drain from the intermediate channel into the collection bag.

The present subject matter, thus discloses a safe and economical ostomy management device. In one example, the ostomy port may be left in an inserted position for long durations, for example, from 15 days to 45 days, thus improving the quality of life for the patient. Further, since the stoma plug can be used to cover the stoma, the ostomy management device makes patient's life easier in terms of not having to carry a removable bag. Further, providing the stoma guide makes the ostomy management device easy to install. Further, providing the instilling fluid in the outer flange facilitates in eliminating the use of external device for installing and removing the ostomy management device as the patient may inflate and deflate the fixation element by simple operation of the outer flange. The patient may thus apply the ostomy management device on his own, i.e., without requiring any assistance from a medical person. As described above, the ostomy management device can be used by the patient after the ostomy surgery for self application. In one example, healthcare professionals, such as a nurse or a clinic staff may provide help and guidance to the patient while the patient applies the ostomy management device.

FIG. 1 illustrates a block diagram of an ostomy management device, in accordance with an embodiment of the present subject matter. In one example, the ostomy management device 100 can be used by an ostomate, interchangeably referred to as patient or a user, after an ostomy surgery. In the embodiment, the ostomy management device 100, hereinafter referred to as the device 100, includes an ostomy port 102, a stoma guide 104, a stoma plug 106, and a collection bag 108.

The ostomy port 102 may be inserted inside patient's abdomen through the stoma, such that a proximal end of the ostomy port 102 enters the abdomen of the patient, while the distal end of the ostomy port 102 gets affixed to a periphery of the stoma. In one example, the ostomy port 102 may be made of a soft flexible biocompatible material that cause no side-effect or allergy to the patient. The ostomy port 102 includes an outer flange (not shown in the figure), an intermediate channel (not shown in the figure), and a fixation element (not shown in the figure). The outer flange is located at a distal end of the ostomy port 102, i.e., the end that is away from the patient's centre of body. The outer flange may be made of a transparent material and is placed such that the outer flange covers the periphery of a stoma of a patient in flush with skin of the patient. The outer flange includes a collapsible chamber to collect instilling fluid in a non-operating state of the outer flange. In one implementation, the collapsible chamber is connected to the fixation element through a fluid pathway in the intermediate channel such that on compression of the collapsible chamber, the instilling fluid gets displaced from the collapsible chamber and moves into the fixation element. The outer flange may further include a snap fit mechanism to hold the outer flange in a compressed position preventing any accidental deflation of the fixation element.

The fixation element is positioned inside the patient's body at a proximal end of the ostomy port 102, i.e., the end towards the patient's centre of body. In one implementation, the fixation element is made of a toroid shaped balloon provided along the proximal end of the intermediate channel, i.e., the end near to the centre of the body of the patient. In one example, the fixation element is placed such that it expands within the intestine, for a lesser diameter within the abdominal wall to provide sealing. In another example, the fixation element is placed such that it expands within the intestine for a greater diameter within a peritoneal cavity thereby anchoring against the inner lining of the peritoneal cavity. Further, the volume of instilling fluid can be varied in order to accommodate any variations in the thickness in abdominal wall for effective anchorage.

The intermediate channel may be a tubular structure adapted for transporting body waste out of the distal end of the ostomy port 102. In one example, the intermediate channel is made of such material so as to accommodate the peristaltic waves generated by the intestine of the patient. In one implementation, the intermediate channel may include a fluid pathway to allow flow of instilling fluid from the collapsible chamber to the fixation element.

In one implementation, the stoma guide 104 may be made of a cylindrical structure wide enough to accommodate the ostomy port 102 described above. The tip of the stoma guide 104 is designed so as to facilitate easy entry of the stoma guide 104 into the stoma opening along with the ostomy port 102. Further, the stoma plug 106 may be inserted over the opening of the outer flange to stop the body wastes from pouring out in between evacuations. Furthermore, the collection bag 108 may be made of a plastic material which can be fastened to the ostomy port 102 on the outer side of the flange by means of a connection feature. In one example, the connection feature may be a clip, an elastic band, and the like.

Figure 2A:
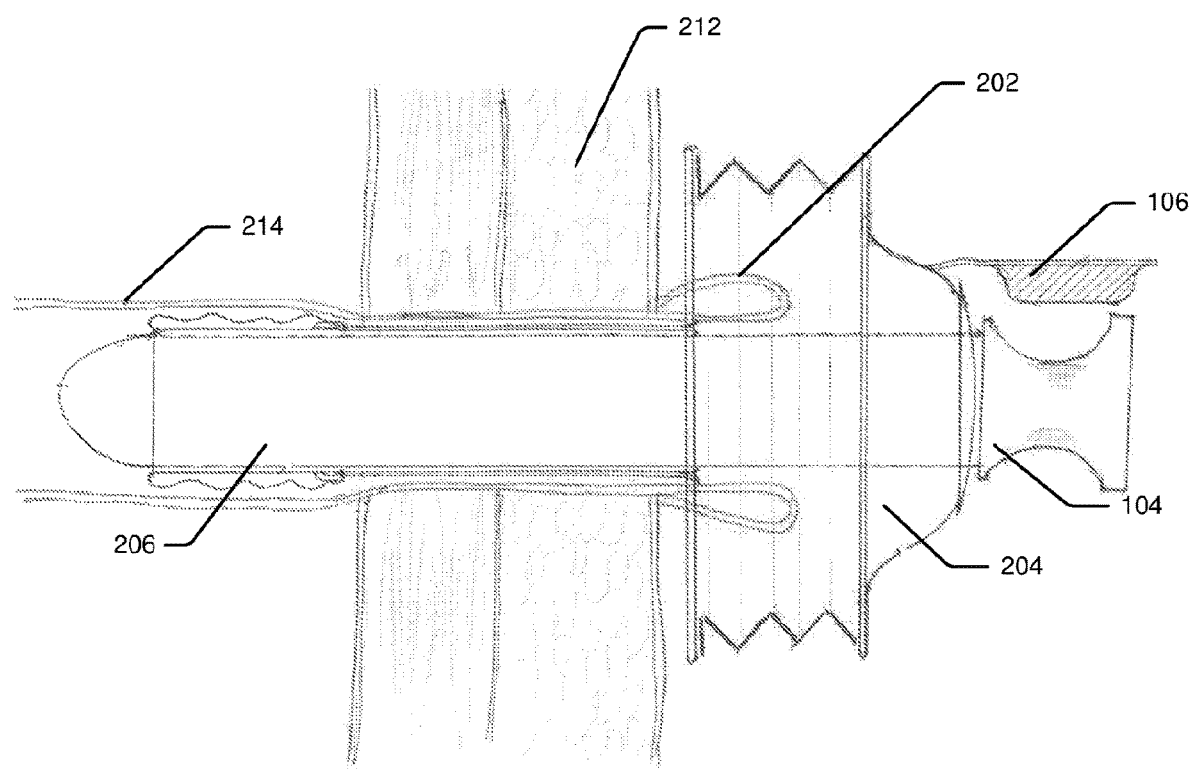
FIGS. 2a, 2b, and 2c illustrate the ostomy management device at different stages of placement of the ostomy management device, in accordance with an embodiment of the present subject matter.
Figure 2B:
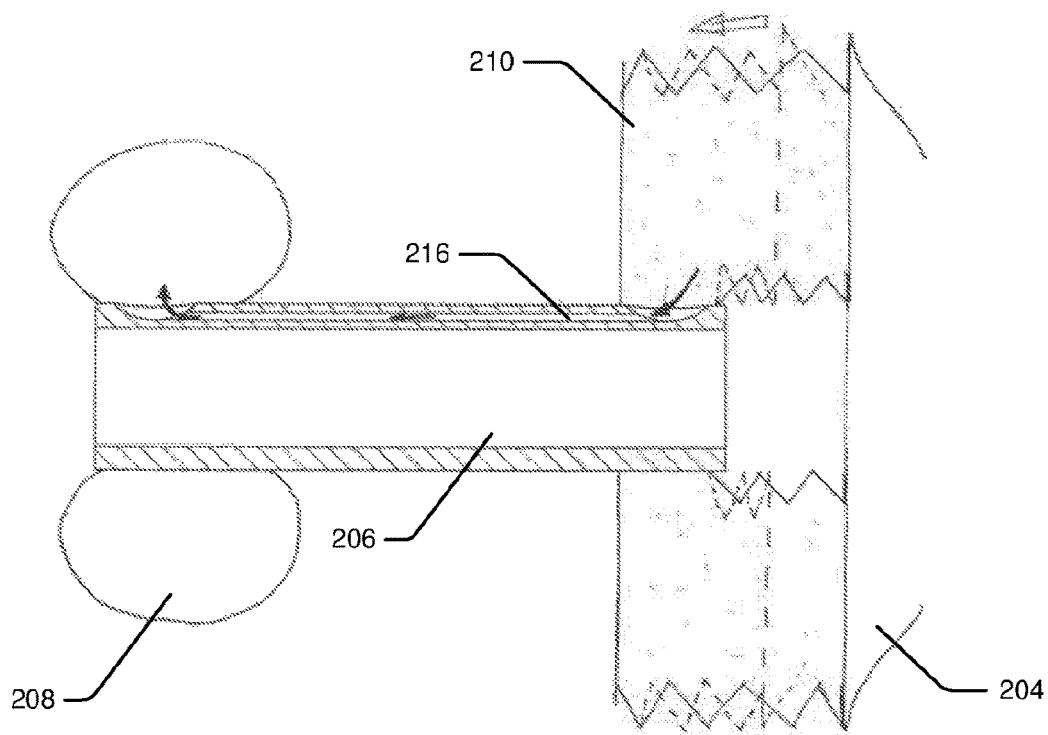
Figure 2C:
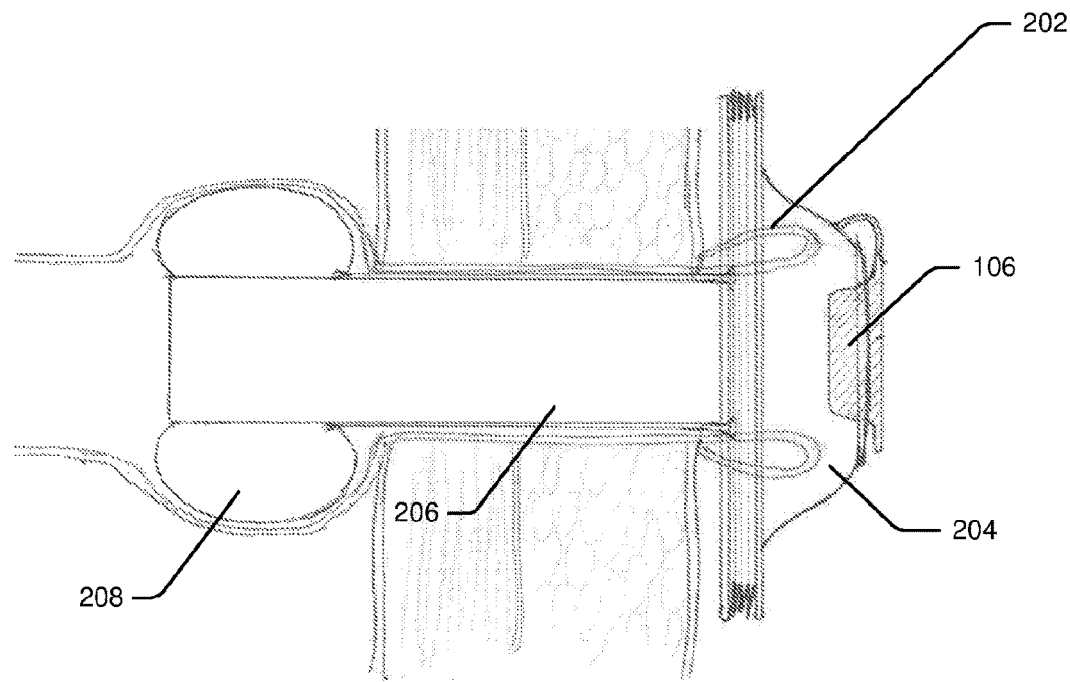

FIGS. 2a, 2b, and 2c illustrate the device 100 at different stages of placement on the patient's stoma 202, in accordance with an embodiment of the present subject matter. FIG. 2a illustrates the device 100 being inserted into a stoma 202 of a patient after the patient has undergone the ostomy surgery or the ostomy procedure. As can be seen in the FIG. 2a, the ostomy port 102 includes an outer flange 204, an intermediate channel 206, and a fixation element 208 in a deflated state. In one implementation, the outer flange 204 includes a plurality of discs and a collapsible bag coupled together to form a collapsible chamber 210 to contain the instilling fluid. The collapsible chamber 210 is in contact with the patient's skin by means of an inner disc from among the plurality of discs. The inner disc includes a soft foam or sponge to reduce discomfort from using the device, as the device may constantly touch the patient's skin. Further, on compression of the plurality of the discs, the instilling fluid is transferred to the fixation element 208.

In one implementation, to insert the device 100 into the stoma 202, the patient may hold the stoma guide 104 and gently insert the tip of the stoma guide 104 protruding through the ostomy port 102 into the stoma 202. Once the ostomy port 102 is advanced into the stoma 202, the patient applies pressure over the outer flange 204 to place and adhere the outer flange 204 on the periphery of the stoma 202. The outer flange 204 adheres to the skin through a mild adhesive base of the outer flange 204. The adhesion between the outer flange 204 and the skin gives an additional support to bear the weight of the collection bag 108. In another implementation, the outer flange 204 may be an elliptical shaped structure placed horizontally to accommodate the skin folds in patients who are obese.

Once the ostomy port 102 is advanced into the stoma 202 and the outer flange 204 has been placed, the patient further applies pressure over the outer flange 204 thus displacing the instilling fluid into the fixation element 208. In one implementation, the fixation element 208 is made from an elastic component and may be placed such that it expands within the layers of the abdominal wall 212 thereby anchoring the device 100. The proximal end of the fixation element 208 helps to maintain a seal between the ostomy port 102 and intestine 214. Further, the distal end of the fixation element 208 anchors the device 100 against abdominal wall 212. In one example, the outer flange 204 may include a battery operated pump to drive the instilling fluid into the fixation element 208. For removing the instilling fluid, the same pump may be operated in reverse direction to drain out the instilling fluid from the fixation element 208. In another embodiment, the instilling fluid contained within the outer flange 204 may be transferred to the fixation element 208 and drained out using a bellow mechanism provided in the collapsible chamber 210.

FIG. 2b illustrates the device 100 in a state of anchoring in the patient's abdomen. As previously described, the ostomy port 102 is advanced into the stoma 202 and the abdomen in a non-operating state of the device 100, during which the instilling fluid is contained inside the collapsible chamber 210 and the fixation element 208 is thus in the deflated state. Once the device 100 is inserted inside the stoma 202, the device 100 may be anchored inside abdomen wall 212 so that the device 100 is securely placed inside the patient's body and does not come off during use. To anchor the device 100, the patient may compress the outer flange 204, thus collapsing the collapsible chamber 210 containing the instilling fluid. Consequently, the instilling fluid displaces from the collapsible chamber 210 to the fixation element 208 through a fluid pathway 216 integrated within the walls of the intermediate channel 206. As illustrated, the fluid pathway 216 runs all along the length of the intermediate channel 206 and connects the distal and proximal ends of the ostomy port 102. Subsequently, the fixation element 208 expands and becomes larger in size than the stoma 202 and anchors the device 100 in the abdomen.

FIG. 2c illustrates the device 100 placed in the stoma 202. Once the device 100 is anchored in the abdomen, the outer flange 204 is further locked and held by a locking means in its compressed state, thereby preventing any accidental deflation of the fixation element 208. In an embodiment, the locking means may be a snap fit mechanism. Further, the patient may retract the stoma guide 104 leaving the ostomy port 102 behind. The patient may then close the ostomy port 102 with the stoma plug 106 attached to the outer flange 204. The stoma plug 106 may be a mechanical type plug or a closed valve type plug that may be integrated to the intermediate channel 206 and that may open upon attachment of the collection bag 108 to the outer flange 204. Additionally, the stoma plug 106 may also include a pressure sensor to monitor the pressure build up inside the intestine 214. The stoma plug 106 may be adapted to open when the pressure inside the intestine 214 exceeds a predefined threshold pressure. This provides a continent device 100 for the patient. The patient can open the stoma plug 106 whenever the patient wants to evacuate the body wastes of the patient. In one example, the body wastes may be evacuated by collecting the body waste in a collection bag 108. In another example, the body wastes may be evacuated by directly draining the body wastes into the toilet. In yet another example, the body wastes may be evacuated by utilizing any other means of forced evacuation, including but not limited to an enema type system. According to one implementation, the patient may attach the collection bag 108 to the ostomy port 102 by connecting it to the outer flange 204. Once the collection bag 108 is locked in place, the patient may carry out normal activities until the collection bag 108 gets filled and needs to be emptied or changed.

Figure 3A:
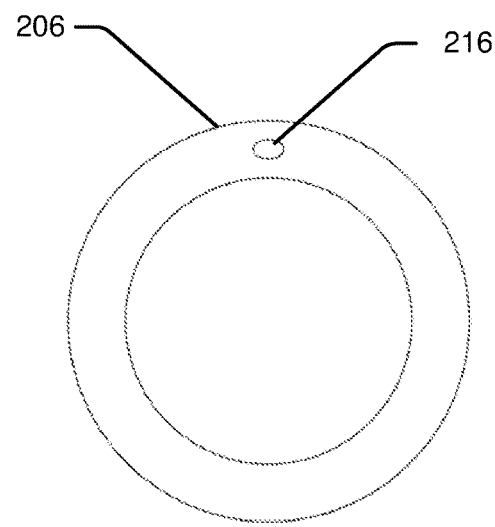
FIGS. 3a and 3b, illustrate front and perspective views of the intermediate channel, in accordance with an embodiment of the present subject matter.
Figure 3B:
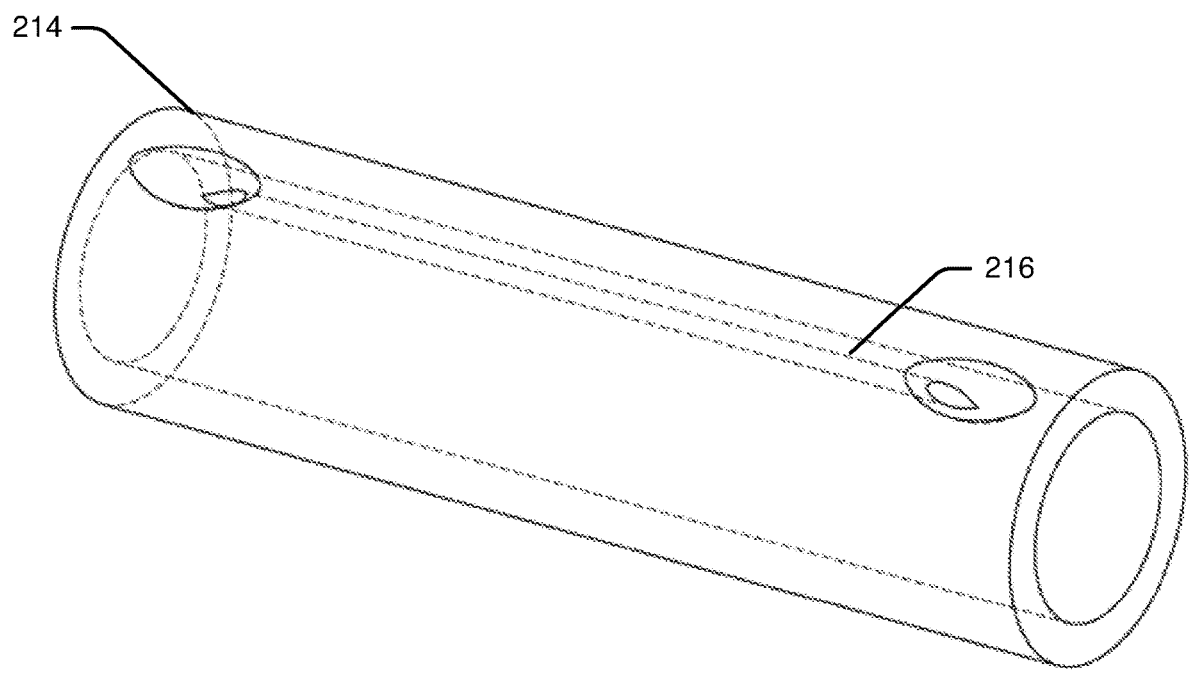

FIGS. 3a and 3b illustrate front and perspective views of the intermediate channel 206 having a fluid pathway 216, in accordance with an embodiment of the present subject matter. As illustrated in FIG. 3a, the fluid pathway 216 is integrated within the wall of the intermediate channel 206. The fluid pathway 216 runs along the length of the intermediate channel 206 and terminates on both sides at the proximal and the distal ends of the intermediate channel 206. As previously described, the proximal end of the fluid pathway 216 is enclosed by the fixation element 208 and the distal end of the fluid pathway 216 is enclosed by the collapsible chamber 210. FIG. 3b illustrates a perspective view of the fluid pathway 216 integrated within the walls of the intermediate channel 206, according to one implementation of the present subject matter.

Figure 3C:
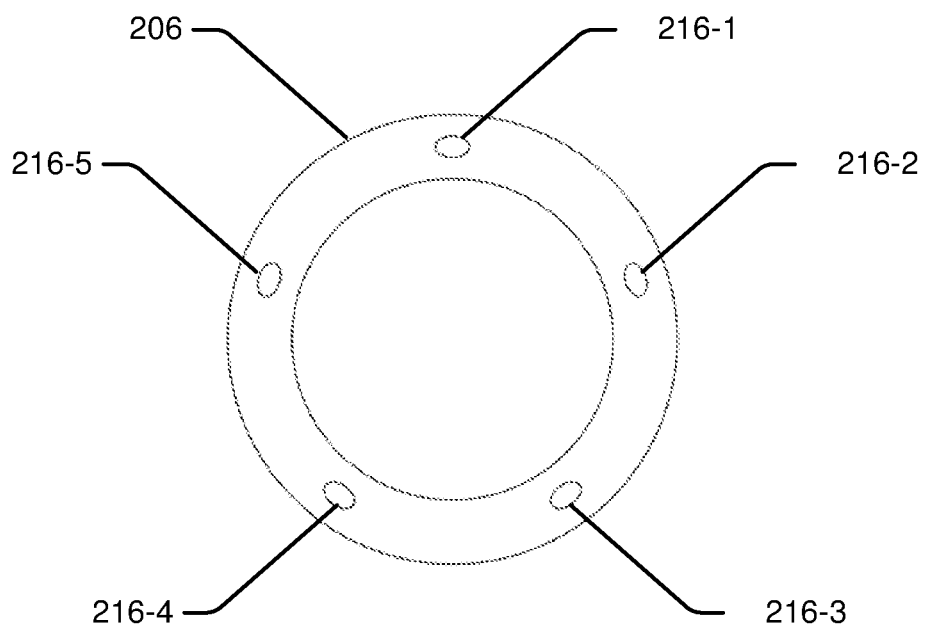
FIG. 3c, illustrates a front view of the intermediate channel, in accordance with an embodiment of the present subject matter.

FIG. 3c illustrates the intermediate channel 206 including a plurality of fluid pathways 216-1 to 216-5 within the wall of the intermediate channel 206. The plurality of fluid pathways would ensure that the collapsible chamber 210 is always connected to the fixation element 208, as a single fluid pathway may get blocked due to peristaltic waves of the intestine 214. Therefore, a plurality of fluid pathways 216-1 to 216-5 ensures that the collapsible chamber 210 is always connected to the fixation element 208 for ready installation and removal of the device 100.

Figure 4A:
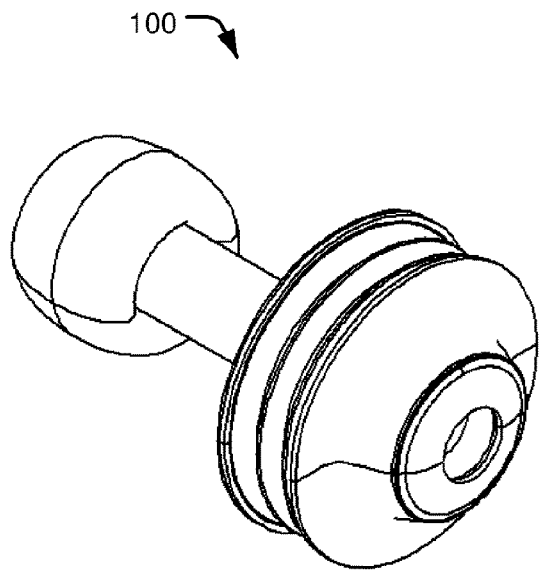
FIGS. 4a, 4b, and 4c illustrate different views of the ostomy management device, in accordance with an embodiment of the present subject matter.
Figure 4B:
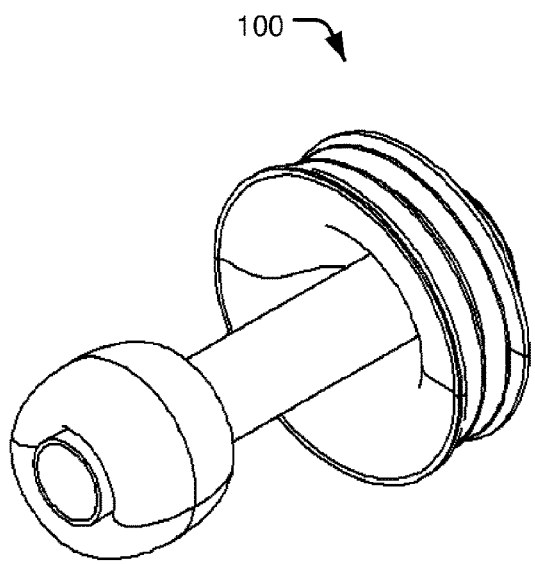
Figure 4C:
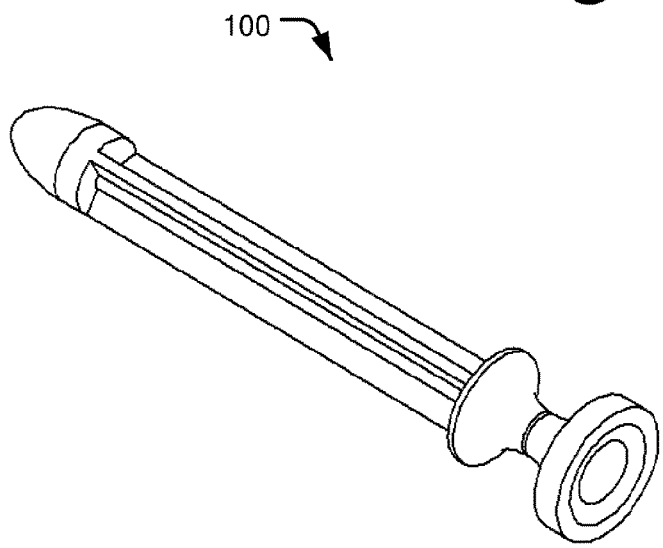

FIGS. 4a and 4b illustrate isometric views of the ostomy management device 100, in accordance with an embodiment of the present subject matter. FIG. 4c illustrates an isometric view of the stoma guide 104, in accordance with an embodiment of the present subject matter.

Figure 5A:
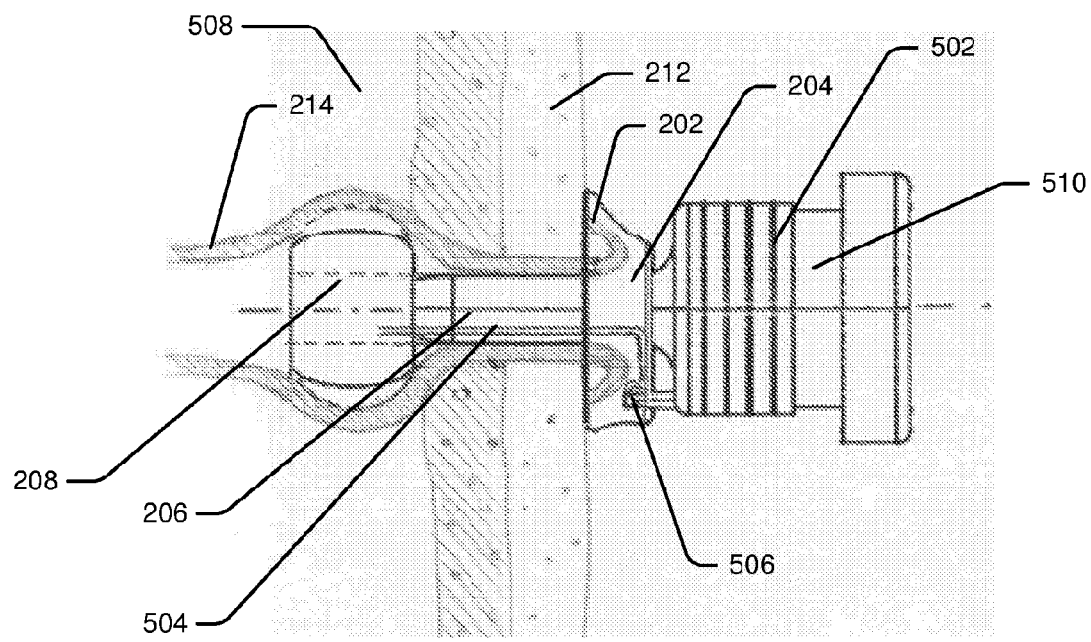
FIGS. 5a, 5b, and 5c illustrate the ostomy management device at different stages of placement and functioning of the ostomy management device, in accordance with another embodiment of the present subject matter.

FIG. 5a illustrates the device 100, in accordance with another embodiment of the present subject matter. In the embodiment, the device 100 includes the ostomy port 102, an applicator 502, and the collection bag 108. The ostomy port 102 includes the outer mushroom shaped cover with the outer flange 204, the intermediate channel 206, and the fixation element 208. In one example, the ostomy port may be made of a soft flexible biocompatible material. Further, the outer flange 204 is made of a transparent material and is placed such that the outer flange 204 covers a stoma 202 of a patient in flush with skin of the patient. The device 100 also includes an inlet port 504 to instill air or fluid into the fixation element 208 after the inlet port 504 is aligned with the applicator 502. The inlet port 504 includes a valve 506 which, on activation, allows for instilling fluid, such as air or fluid through the intermediate channel 206 into the fixation element 208. In one example, the valve 506 may be a one-way valve.

According to the embodiment, the intermediate channel 206 is a tubular structure adapted to transport the body waste out of a distal end of the ostomy port. The intermediate channel 206 may be made of such a material so as to accommodate peristaltic waves generated by the intestine 214. The intermediate channel 206 also accommodates the fluid pathway 216. The fluid pathway 216 connects the fixation element 208 to the inlet port 504 on the outer flange 204. According to an example, the fixation element 208 is made of a toroid shaped elastic component filled with a fluid, such as air, water, saline or any biocompatible fluid. The fixation element 208 may be placed such that it expands within the intestine 214 after traversing the abdominal wall 212 thereby anchoring against an inner surface of a peritoneal cavity 508. In an example, the volume of instilling fluid may be varied in order to accommodate any variations in the thickness in abdominal wall 212 for effective anchorage.

Further, the applicator 502 may be made of a cylindrical structure wide enough to accommodate the ostomy port 102 described above, at one end. Towards the distal end, the applicator 502 may house a chamber containing the instilling fluid with a plunger 510 to displace the instilling fluid contained in the chamber. Moreover, the applicator 502 may also include a nozzle which connects with the inlet port 504 in the ostomy port 102, and allows the instilling fluid to be transferred from the applicator 502 to ostomy port 102 to facilitate the inflation of the fixation element 208.

As described above, the device 100 may include the collection bag 108. The collection bag 108 may be made of a plastic inner lining with a microfiber outer layer. The inner lining may be designed so as to snuggly fit the opening of the ostomy port to avoid spoiling of the outer surface of the ostomy port. The outer layer of the collection bag 108 may be made of microfiber clothing to absorb sweat and also to prevent irritation of the skin around the stoma 202. According to an example, the collection bag 108 may be fastened on to the ostomy port 102 by means of a connection member. In one example, the connection member may be a clip, an elastic band, or any other means known in the art.

Figure 5B:
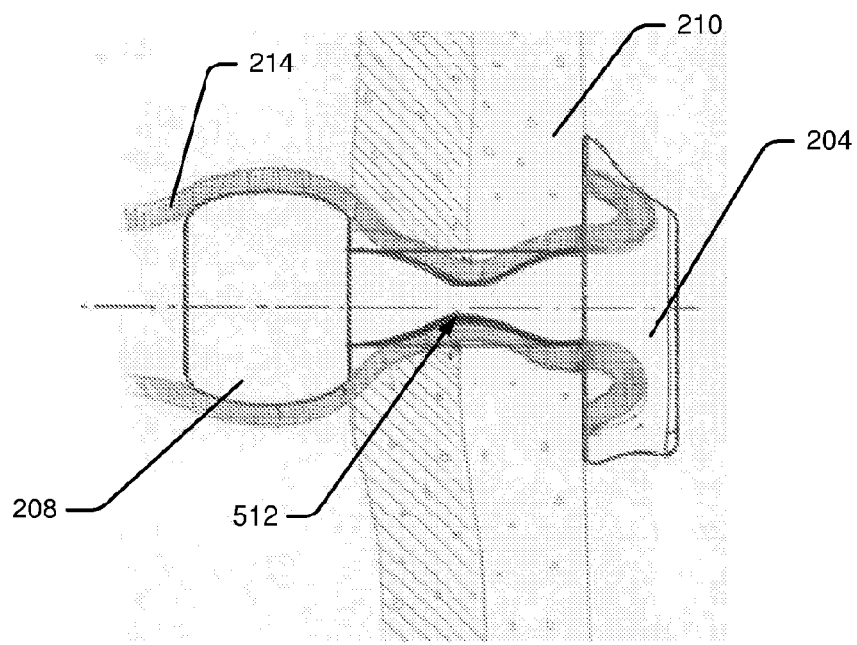
Figure 5C:
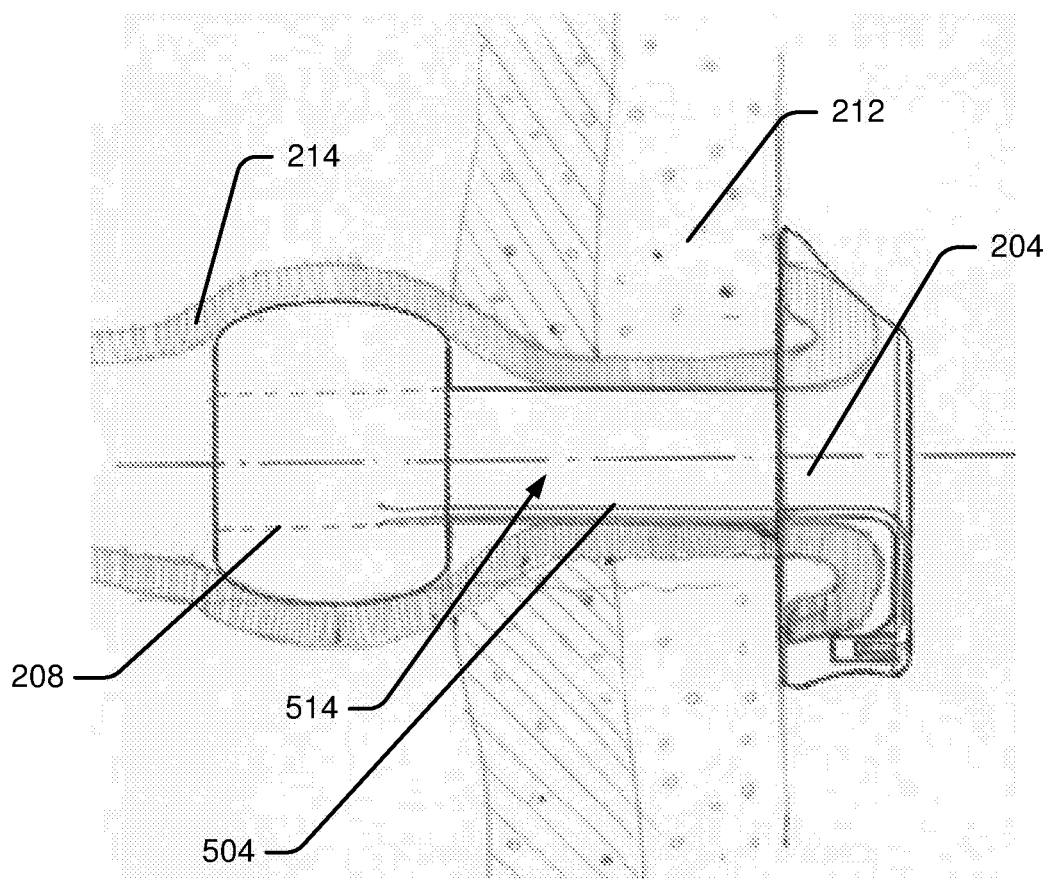

FIG. 5b illustrates a pliable intermediate channel 206 during peristalsis, as depicted by an arrow 512. FIG. 5c illustrates the intermediate channel 206 in-between peristalsis as depicted by an arrow 514.

Figure 6A:
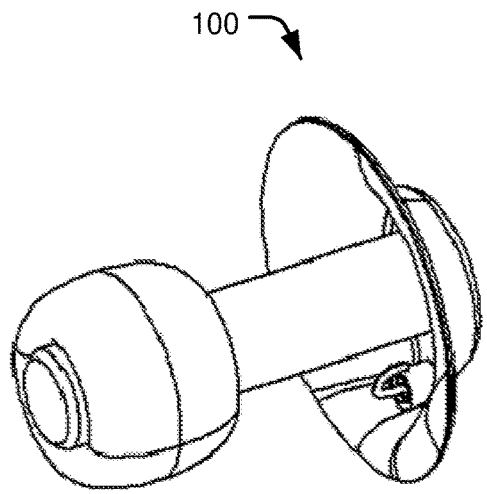
FIGS. 6a, 6b, and 6c illustrate different views of the ostomy management device, in accordance with another embodiment of the present subject matter.
Figure 6B:
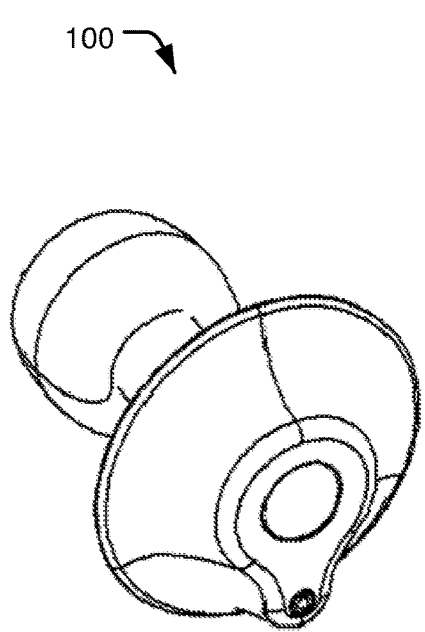
Figure 6C:
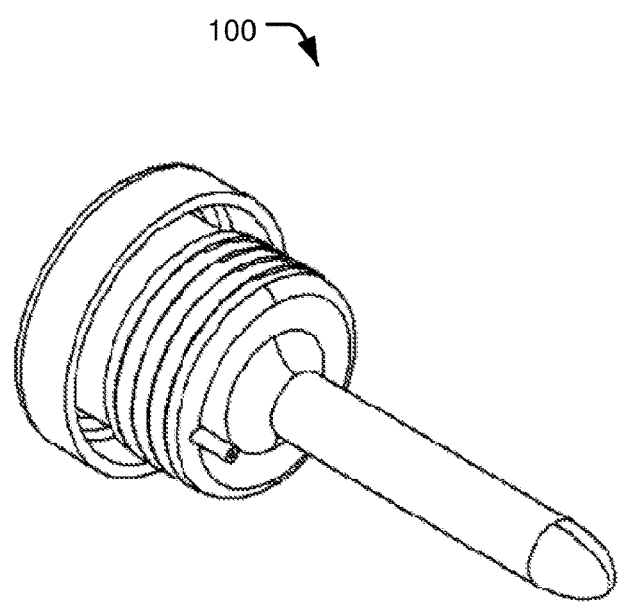

FIGS. 6a and 6b illustrate isometric views of the ostomy management device 100, in accordance with another embodiment of the present subject matter. The ostomy management device 100 provides the ostomy port 102 that can be easily and safely inserted into the stoma 202 and held in place without an external source of fluid. According to the present subject matter, the ostomy management device 100 provides a safe and easy method for allowing the body waste to exit from the body after the ostomy surgery. FIG. 6c illustrates an isometric view of the applicator 502, in accordance with another embodiment of the present subject matter.

Although implementations of the ostomy management device 100 have been described in language specific to structural features, it is to be understood that the subject matter is not necessarily limited to the specific features described. Rather, the specific features are disclosed as implementations for the ostomy management device 100.

We claim:

1. An ostomy management device comprising:
   an ostomy port insertable inside a stoma on a patient's abdomen, the ostomy port comprising:
   a fixation element to anchor the ostomy management device inside an intestine once the ostomy port is inserted into the intestine of the patient, through the stoma, wherein the fixation element is to inflate to anchor the ostomy management device inside the intestine, and wherein the fixation element is to deflate to allow removal of the ostomy management device from the intestine; and
   an outer flange placed at periphery of the stoma to inflate and deflate the fixation element, wherein the outer flange comprising:
   a collapsible chamber comprising a plurality of discs and a collapsible bag coupled together to collect instilling fluid in a non-operating state of the outer flange;
   wherein the plurality of discs and the collapsible bag are fixed to one another to remain coupled together as the collapsible chamber at least while the ostomy management device is anchored inside the intestine of the patient, through the stoma,
   wherein a user compresses the outer flange to displace the instilling fluid to the fixation element to inflate the fixation element,
   wherein the user operates the outer flange to drain out the instilling fluid from the fixation element to the collapsible chamber, to deflate the fixation element for removing the ostomy port; and
   wherein the collapsible chamber is to retain the instilling fluid in the non-operating state of the outer flange after the instilling fluid is drained out to the collapsible chamber from the fixation element;
   an intermediate channel connecting a distal end of the ostomy port to the proximal end to transport body waste from the intestine to the stoma; and
   a stoma plug, attached to the outer flange, to cover an opening in the outer flange to stop the body waste from flowing out from the stoma during an operating state of the outer flange.

2. The ostomy management device as claimed in claim 1, wherein the intermediate channel further comprises at least one fluid pathway connecting the collapsible chamber to the fixation element to allow flow of the instilling fluid from the collapsible chamber to the fixation element upon compression of the outer flange.

3. The ostomy management device as claimed in claim 1, wherein the plurality of discs and the collapsible bag are fixedly coupled together to provide a bellows mechanism operable for containing and displacing the instilling fluid.

4. The ostomy management device as claimed in claim 3, wherein the collapsible chamber is to collapse upon compression of the plurality of discs to displace the instilling fluid to the fixation element.

5. The ostomy management device as claimed in claim 3, wherein the ostomy port further includes a snap fit locking means to lock and hold the outer flange in the compressed position during the operating state of the outer flange.

6. The ostomy management device as claimed in claim 5, wherein upon unlocking of the snap fit locking means, the outer flange is to decompress to drain out the instilling fluid from the fixation element to the outer flange, to deflate the fixation element such that the ostomy port may be retracted out of the stoma.

7. The ostomy management device as claimed in claim 1, wherein the stoma plug includes a closed valve type plug that is to open upon connection of a collection bag to the outer flange.

8. The ostomy management device as claimed in claim 7, wherein the closed valve type plug further includes a pressure sensor to monitor the pressure inside the intestine so that the closed valve is to open when the pressure inside the intestine exceeds a predefined threshold.

9. The ostomy management device as claimed in claim 1, wherein the ostomy management device further comprises a stoma guide to be placed inside the intermediate channel to guide the ostomy port inside the stoma.

10. The ostomy management device as claimed in claim 1, wherein the ostomy management device comprises the collection bag, connectable to the outer flange, to collect the body waste flowing out of the distal end of the ostomy port through the intermediate channel.

11. An ostomy management device at least a portion of which is insertable inside a stoma on an abdomen of a patient to provide a fluid passage with an intestine of the patient, the ostomy management device comprising:

an ostomy port comprising: a fixation element, an outer flange, an intermediate channel, and having a distal end and a proximal end, the fixation element insertable through the stoma to be positioned in the intestine of the patient and selectively inflatable to anchor the portion of the ostomy management device inside the intestine of the patient, and selectively deflatable to subsequently allow removal of the portion of the ostomy management device from the intestine of the patient; the outer flange comprising a plurality of discs and a collapsible bag fixedly coupled to the plurality of discs to form a collapsible chamber, and the intermediate channel fluidly communicatively coupling an interior of the fixation element with an interior of the collapsible chamber, wherein the collapsible chamber is physically manipulable from an exterior of the body of the patient to drive an instilling fluid from the interior of the collapsible chamber into the interior of the fixation element to inflate the fixation element and thereby anchor the portion of the ostomy management device inside the intestine of the patient and wherein the collapsible chamber is physically manipulable from the exterior of the body of the patient to drive the instilling fluid from the interior of the fixation element into the interior of the collapsible chamber to deflate the fixation element and thereby unanchor the portion of the ostomy management device from the inside of the intestine of the patient to allow removal of the ostomy management device while retaining the instilling fluid in the interior of the collapsible chamber;

an intermediate channel connecting the distal end of the ostomy port to the proximal end of the ostomy port to transport body waste from the intestine through the stoma; and a stoma plug, attached to the outer flange, to selectively block the intermediate channel to stop the body waste from flowing out from the stoma via the intermediate channel.

* * * * *